(12) United States Patent
Ainciburu et al.

(10) Patent No.: US 8,486,632 B2
(45) Date of Patent: Jul. 16, 2013

(54) METHOD FOR THE IN VITRO DIAGNOSIS OF BRONCHOPULMONARY CARCINOMA BY DETECTION OF MAJOR ALTERNATIVE TRANSCRIPTS OF THE KLK8 GENE ENCODING KALLIKREIN 8 AND USE THEREOF FOR PROGNOSTICATING SURVIVAL

(75) Inventors: Mireille Ainciburu, Sussargues (FR); Yves Courty, Tours (FR); Colette Jolivet-Reynaud, Saint Bonnet de Mure (FR); Chris Planque, Pornichet (FR)

(73) Assignees: Biomerieux, Marcy l'Etoile (FR); Universite Francois Rabelais, Tours (FR)

( * ) Notice: Subject to any disclaimer, the term of this patent is extended or adjusted under 35 U.S.C. 154(b) by 0 days.

(21) Appl. No.: 13/535,136

(22) Filed: Jun. 27, 2012

(65) Prior Publication Data
US 2012/0295261 A1 Nov. 22, 2012

Related U.S. Application Data

(62) Division of application No. 12/310,622, filed as application No. PCT/FR2007/052023 on Sep. 27, 2007, now Pat. No. 8,236,506.

(30) Foreign Application Priority Data

Sep. 28, 2006 (FR) ...................................... 06 53983

(51) Int. Cl.
*C12Q 1/68* (2006.01)
*C07H 21/02* (2006.01)
*C07H 21/04* (2006.01)
(52) U.S. Cl.
USPC ......... 435/6.11; 435/6.1; 435/6.14; 435/6.16; 435/6.18; 536/23.2; 536/23.5; 536/24.3
(58) Field of Classification Search
None
See application file for complete search history.

(56) References Cited

U.S. PATENT DOCUMENTS

| 4,672,040 | A | 6/1987 | Josephson |
| 4,683,195 | A | 7/1987 | Mullis et al. |
| 4,683,202 | A | 7/1987 | Mullis |
| 4,800,159 | A | 1/1989 | Mullis et al. |
| 4,981,783 | A | 1/1991 | Augenlicht |
| 5,234,809 | A | 8/1993 | Boom et al. |
| 5,399,491 | A | 3/1995 | Kacian et al. |
| 5,445,934 | A | 8/1995 | Fodor et al. |
| 5,700,637 | A | 12/1997 | Southern |
| 5,744,305 | A | 4/1998 | Fodor et al. |
| 5,750,338 | A | 5/1998 | Collins et al. |
| 5,807,522 | A | 9/1998 | Brown et al. |
| 8,236,506 | B2 * | 8/2012 | Ainciburu et al. ........... 435/6.14 |

| 2004/0033516 | A1 | 2/2004 | Mougin |
| 2006/0205054 | A1 | 9/2006 | O'Brien et al. |
| 2010/0255466 | A1 | 10/2010 | Ainciburu et al. |

FOREIGN PATENT DOCUMENTS

| EP | 0 201 184 A2 | 12/1986 |
| FR | 2 816 711 A1 | 5/2002 |
| FR | 2 816 958 A1 | 5/2002 |
| WO | WO 89/10977 | 11/1989 |
| WO | WO 90/01069 | 2/1990 |
| WO | WO 90/03382 | 4/1990 |
| WO | WO 90/06995 | 6/1990 |
| WO | WO 91/02818 | 3/1991 |
| WO | WO 94/12670 | 6/1994 |
| WO | WO 97/45202 | 12/1997 |
| WO | WO 99/15321 | 4/1999 |
| WO | WO 99/35500 | 7/1999 |
| WO | WO 99/53304 | 10/1999 |
| WO | WO 00/05338 | 2/2000 |
| WO | WO 00/71750 A1 | 11/2000 |

OTHER PUBLICATIONS

Planque et al. Clinical Chemistry. 2010. 56: 987-997.*
Planque et al.; "Expression of the human kallikrein genes 10 (KLK10) and 11 (KLKI1) in cancerous and non-cancerous lung tissues;" *Biological Chemistry*; Jun. 2006; pp. 783-788; vol. 387; No. 6.
Sher et al.; "Human Kallikrein 8 Protease Confers a Favorable Clinical Outcome in Non-Small Cell Lung Cancer by Suppressing Tumor Cell Invasiveness;" *Cancer Research*; Dec. 2006; pp. 11763-11770; vol. 66; No. 24.
Singh et al.; "Expression of kallikrein-related peptidases (KRP/hk5, 7, 6, 8) in subtypes of human lung carcinoma;" *International Immunopharmacology*; Sep. 2007; pp. 300-306; vol. 8; No. 2.
Magklara et al.; "The Human KLK8 (Neuropsin/Ovasin) Gene: Identification of Two Novel Splice Variants and Its Prognostic Value in Ovarian Cancer;" *Clinical Cancer Research*; Apr. 2001; pp. 806-811; vol. 7; No. 4.
Shigemasa et al.; "Human kallikrein 8 (hK8/TADG-14) expression is associated with an early clinical stage and favorable prognosis in ovarian cancer;" *Oncology Reports*; Jun. 2004; pp. 1153-1159; vol. 4; No. 6.
Planque et al.; "KLK5 and KLK7, two members of the human tissue kallikrein family, are differentially expressed in lung cancer;" *Biochemical and Biophysical Research Communications*; Apr. 2005; pp. 12604266; vol. 329; No. 4.
Yousef et al.; "The New Human Tissue Kallikrein Gene Family: Structure, Function, and Association to Disease;" *Endocrine Reviews*; Apr. 2001; pp. 184-204; vol. 22; No. 2.

(Continued)

*Primary Examiner* — Carla Myers
(74) *Attorney, Agent, or Firm* — Oliff & Berridge, PLC

(57) ABSTRACT

A method for the in vitro diagnosis of bronchopulmonary carcinoma, in particular of non-small cell bronchial carcinoma, that includes a stage of detecting, in a biological sample derived from a patient suspected to be suffering from bronchopulmonary carcinoma, at least one of the major alternative transcripts of the KLK8 gene encoding kallikrein 8. This method is particularly useful for the survival prognostication of patients suffering from bronchopulmonary carcinoma.

7 Claims, 1 Drawing Sheet

OTHER PUBLICATIONS

Bhattacharjee et al.; "Classification of human lung carcinomas by mRNA expression profiling reveals distinct adenocarcinoma subclasses;" *PNAS*; Nov. 2001; pp. 13790-13795; vol. 98; No. 24.

Garber et al.; "Diversity of gene expression in adenocarcinoma of the lung;" *PNAS*; Nov. 2001; pp. 13784-13789; vol. 98; No. 24.

Dong et al.; "Human Kallikrein 4 (KLK4) Is Highly Expressed in Serous Ovarian Carcinomas;" *Clinical Cancer Research*; Aug. 2001; pp. 2363-2371; vol. 7.

Dong et al.; "Differential Splicing of *KLK5* and *KLK7* in Epithelial Ovarian Cancer Produces Novel Variants with Potential as Cancer Biomarkers;" *Clinical Cancer Research*; May 2003; pp. 1710-1720; vol. 9.

Yoshida et al.; "Sequence analysis and expression of human neuropsin cDNA and gene;" *Gene*; 1998; pp. 9-16; vol. 213.

Mitsui et al.; "A novel form of human neuropsin, a brain-related serine protease, is generated by alternative splicing and is expressed preferentially in human adult brain;" *European Journal of Biochemistry*; 1999; pp. 627-634; vol. 260.

Liu et al., "Comparison of differentially expressed genes in T lymphocytes between human autoimmune disease and murine models of autoimmune disease," Clinical Immunology, vol. 112, pp. 225-230, 2004.

Coleman, "Of mouse and man—what is the value of the mouse in predicting gene expression in humans?," Drug Discovery Today, vol. 8, pp. 233-235, 2003.

Schmidt, "Lack of Interferon Consensus Sequence Binding Protein (ICSBP) Transcripts in Human Myeloid Leukemias," Blood, vol. 91, pp. 22-29, 1998.

* cited by examiner

METHOD FOR THE IN VITRO DIAGNOSIS OF BRONCHOPULMONARY CARCINOMA BY DETECTION OF MAJOR ALTERNATIVE TRANSCRIPTS OF THE KLK8 GENE ENCODING KALLIKREIN 8 AND USE THEREOF FOR PROGNOSTICATING SURVIVAL

CROSS-REFERENCE TO PRIOR APPLICATION

This is a divisional of application Ser. No. 12/310,622 filed Mar. 2, 2009, which is a National Stage Application of PCT/FR2007/052023 filed Sep. 27, 2007, and claims the benefit of French Application No. 0653983 filed Sep. 28, 2006. The entire disclosures of the prior applications are hereby incorporated by reference herein in their entirety.

The present invention relates to the field of cancerology. More particularly, the subject of the present invention is a method for the in vitro diagnosis of primary bronchopulmonary carcinoma in a human patient by determination of the presence, beyond a predetermined threshold, of a major transcript of the KLK8 gene of kallikrein 8 in a biological sample derived from that patient.

Primary bronchopulmonary carcinoma is the main cause of death by cancer in man, and this in all the developed countries. Recent data show a clear increase in its incidence in women. The number of new cases per year is estimated at 25,000 in France and at more than 160,000 in the United States, resulting in the death of about 22,000 individuals per year in France and 155,000 in the United States. Worldwide, broncho-pulmonary carcinoma is thought to be responsible for about 900,000 deaths each year, which would correspond to about 18% of the deaths due to cancer. The main etiology of bronchopulmonary carcinoma is tobacco addiction. About 90% of bronchial cancers in men and about 50% in women are attributable to tobacco. Other environmental or occupational factors can also be recognized in bronchial carcinogenesis.

The World Health Organization (WHO) distinguishes between small cell bronchial carcinomas (SCBC), which represent about 20% of cases, and non-small cell bronchial carcinomas (NSCBC) which inter alia include epidermoid carcinomas, adenocarcinomas, and large cell carcinomas, and which represent about 80% of cases. The epidermoid carcinomas and adenocarcinomas are the most widespread carcinomas.

At the present time, the diagnosis of bronchopulmonary carcinoma is essentially made by pulmonary radiography and thoracic scanning. Bronchial endoscopy making it possible to perform biopsies then confirms the diagnosis. Unfortunately, the indicative symptoms are delayed and not very specific, and the diagnosis is reached at a late stage, thus greatly reducing the efficacy and the feasibility of the existing treatments. In addition, this type of diagnosis requires sophisticated equipment and qualified personnel which is expensive.

Various treatment methods are currently available: surgery, chemotherapy and radiotherapy. These treatments can be carried out either in isolation or consecutively or in combination.

The survival rate for lung cancer is very dependent on the degree of dissemination of the tumor at the time of diagnosis. The overall survival rate at 5 years is of the order of 15%. However, this rate masks substantial disparities. The survival rate of patients having a carcinoma with remote metastasis at the time of diagnosis is less than 5% whereas patients whose "non-small cell carcinoma" (NSCBC) is localized at the time of its discovery exhibit survival rates close to 50%[1]. These latter are essentially treated by surgical resection of the tumor, an approach which for the time being represents the only curative solution for this type of carcinoma. However, fewer than one patient in 3 can receive such treatment and one patient in 2 treated surgically dies in the months following the operation, following a tumor relapse. Recent progress in the field of the modern chemotherapy of NSCBC makes it possible to envisage adjuvant or neo-adjuvant treatments improving the life expectation of the patients who have undergone surgery[2]. However, such treatments are not trivial, with an associated mortality rate which is not negligible. In this context, it is important to be able to identify the operable patients exhibiting a high risk of death due to relapse, in order to facilitate the decision whether or not to give neo-adjuvant or adjuvant chemotherapy.

Markers which make it possible to distinguish tumor cells from healthy cells have been sought and studied for years for all carcinomas and in particular broncho-pulmonary carcinoma. They would make it possible to diagnose the disease at an early stage, to establish its prognosis and sensitivity to treatment, and to monitor its progression. In recent years, more than 100 candidates have been suggested as molecular markers for diagnosis of bronchopulmonary carcinoma. The studies have thus envisaged the diagnostic roles of proto-oncogenes, factors involved in the cell cycle, apoptosis or angiogenesis. However, it has been possible to obtain few correlations between the results obtained by different techniques and validations between various cohorts of patients depending on the technique used (immunohistochemistry, immunological assay, DNA chips utilizing various algorithms) and the great diversity of the tumors (histological type, stage, degree of differentiation).

Other markers, belonging to a subfamily of serine proteases, the kallikreins, of which there are 15, have also been tested. Thus in a study using DNA chips, the hKLK11 gene was identified as a marker of endocrine adenocarcinomas of the C2 type[3]. A similar study has shown that the hKLK5 and hKLK10 genes are overexpressed in epidermoid carcinomas[4]. Similarly, it has been shown that the hKLK5 and hKLK7 genes, respectively encoding the proteins hK5 and hK7, were overexpressed in the tumor tissues of epidermoid carcinomas, while underexpression of the hKLK7 gene in the tumor tissues is most often observed in patients exhibiting an adenocarcinoma[5]. However, it has not been possible to establish any link between the differential expression of these hKLK genes and a survival prognosis for patients suffering from bronchopulmonary carcinoma.

The genes of the 15 kallikreins exhibit characteristics in common, among them the presence of several transcripts for the same gene. The transcripts of these genes have also been studied as markers. Thus, it has been shown that three alternative transcripts of the hKLK4[6] and hKLK5[7] genes, and one transcript of the hKLK7[7] gene were overexpressed in the tumors and/or in ovarian cell lines in comparison with non-cancerous tissue.

It is known that the expression profile of the hKLK8 gene gives rise to at least 4 different transcripts, called NT1 to NT4. The transcript NT1 or "neuropsin type 1", identified by Yoshida S. et al[8], encodes a preproenzyme of 260 amino acids containing a secretion signal peptide of 28 amino acids and a very short prosegment of 4 residues which has to be cleaved off to liberate the active form of kallikrein 8. NT1 is regarded as the regular expression form of the gene. The transcript NT2 or "neuropsin-T2", identified by Mitsui S. et al[9], is differentiated from the NT1 form by the insertion of a sequence encoding 45 supplementary amino acids in the carboxy terminal region of the signal peptide. The transcripts NT3 and NT4 were identified by Magklara A. et al[10] and encode proteins containing respectively 119 and 32 residues. The protein form predicted from NT3 only possesses one part of the signal peptide of kallikrein 8 and does not conserve the cleavage zone of the latter. The protein predicted from NT4 is made up of the first 23 residues of the signal peptide of kallikrein 8 and of 9 supplementary residues with no identity with kallikrein 8. Magklara A. et al[10] have shown that, although the regular expression form of the KLK8 gene, NT1, may be of prognostic value in the context of carcinoma of the ovary, the forms NT3 and NT4 are of no value.

Figure 1:
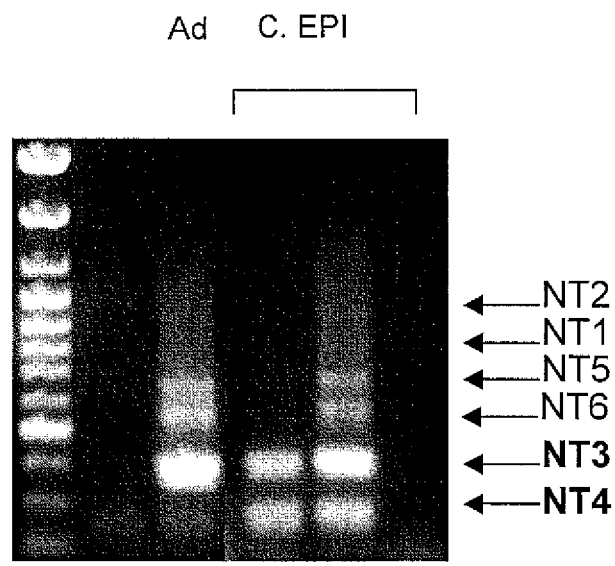
FIG. 1 is a photograph of an electrophoresis gel showing the various alternative transcripts of the KLK8 gene NT1 to NT6 obtained from cancerous tissues of patients suffering from adenocarcinoma (Ad) or epidermoid carcinoma (C. EPI), the left-hand track corresponding to the molecular weight marker track.

The Applicants have now surprisingly shown that the major alternative transcripts of the KLK8 gene encoding kallikrein 8, selected from NT3 and NT4, at a high level, were a good diagnostic marker, and in particular an adverse prognosis marker, in the context of bronchopulmonary carcinomas, and in particular of non-small cell bronchial carcinomas.

Thus, the first subject of the present invention is a method for the in vitro diagnosis of bronchopulmonary carcinoma, in particular of non-small cell bronchial carcinoma, characterized in that it comprises or consists in the stage of detection, in a biological sample derived from a patient suspected to be suffering from said broncho-pulmonary carcinoma, of at least one of the major alternative transcripts of the KLK8 gene of kallikrein 8.

The method of the invention thus makes it possible to establish a diagnosis in the context of bronchopulmonary carcinoma by a simple test consisting in detecting the major alternative transcripts of the KLK8 gene, in particular at a high level.

Alternative transcript of the KLK8 gene is understood to mean the transcription products of the KLK8 gene. Such transcripts are such as described above and are in particular called NT1, NT2, NT3 and NT4. As will be seen later, the Applicants have discovered two new transcripts named NT5 and NT6.

Major transcript is understood to mean the transcripts mainly produced from the gene for expression of the kallikrein 8. According to one implementation mode, the major alternative transcripts of the KLK8 gene are selected from the transcripts NT3 and NT4.

High level of major transcript is understood to mean a level greater than a defined threshold value.

It is known that, in general, the results of tests for detection of analytes to a large extent depend on the characteristics of the binding partners utilized. Thus, for example, in the case of the detection of RNA by hybridization with nucleotide probes, the results in particular depend on the characteristics of size, composition and percentage complementarity of the probes, and that these characteristics influence the values measured with these probes. Thus it follows that it is not possible to give precise threshold values and that the threshold values suitable for each binding partner utilized can be determined in each case by simple routine experiments.

It must be clearly understood that either a discrete value, or a range of values corresponding to a zone of indeterminacy, is referred to here as a threshold value. Quite obviously, when the measured value lies within the indeterminacy interval, or is very close to the threshold value in the case of a discrete value, no definite conclusion can be reached, and further investigations should be carried out.

The biological samples in which the method of the invention is carried out are any biological sample capable of containing major alternative transcripts of the KLK8 gene. As examples of such samples, solid samples such as tissue deriving from the biopsy of the tumor, lymphatic ganglia, metastases from the patient, biological liquids such as blood, serum, plasma and expectorations, and cells purified from these solid or liquid samples, can be cited.

Detection of transcript, in particular of the major alternative transcript, is understood to mean either the direct detection of the transcript, or the indirect detection of the transcript, or any other method for determination of the presence of an RNA in a sample, known to the person skilled in the art.

Direct detection of the transcript, in particular of the major alternative transcript, is understood to mean the detection of said transcript itself in the biological sample.

The direct detection of the major alternative transcript in the biological sample can be carried out by any means known to the person skilled in the art, such as for example by hybridization with a specific binding partner of the major alternative transcript, if necessary after amplification by the PCR or NASBA technique.

Hybridization is understood to mean the process in the course of which, under appropriate conditions, two nucleotide fragments bind together with stable and specific hydrogen bonds to form a double-stranded complex. These hydrogen bonds form between the complementary bases adenine (A) and thymine (T) (or uracil (U)) (referred to as A-T bonding) or between the complementary bases guanine (G) and cytosine (C) (referred to as G-C bonding) The hybridization of two nucleotide fragments can be total (then referred to as complementary nucleotide fragments or sequences), in other words the double-stranded complex obtained during this hybridization contains only A-T bonds and C-G bonds. This hybridization can be partial (then referred to as sufficiently complementary nucleotide fragments or sequences), in other words the double-stranded complex obtained contains A-T bonds and C-G bonds making it possible to form the double-stranded complex, but also bases not bound to a complementary base. The hybridization between two nucleotide fragments depends on the operating conditions which are utilized and in particular on the stringency. The stringency is in particular defined in terms of the base composition of the two nucleotide fragments, as well as by the degree of mismatching between two nucleotide fragments. The stringency can also be a function of the reaction parameters such as the concentration and the type of ionic species present in the hybridization solution, the nature and the concentration of denaturing agents and/or the hybridization temperature. All these data are well known and the appropriate conditions can be determined by the person skilled in the art. In general, depending on the length of the nucleotide fragments which it is desired to hybridize, the hybridization temperature lies between about 20 and 70° C., in particular between 35 and 65° C. in a saline solution at a concentration of about 0.5 to 1M. A sequence, or nucleotide fragment, or oligonucleotide, or poly-nucleotide, is a chain of nucleotide units linked together by phosphate ester linkages, characterized by the information sequence of the natural nucleic acids, capable of hybridizing with a nucleotide fragment, it being possible for the chain to contain monomers of different structures and to be obtained from a natural molecule of nucleic acid and/or by genetic recombination and/or by chemical synthesis. A unit is derived from a monomer which can be natural nucleic acid nucleotide the constituent elements whereof are a sugar, a phosphate group and a nitrogenous base; in DNA the sugar is desoxy-2-ribose, in RNA the sugar is ribose; depending on whether DNA or RNA is involved, the nitrogenous base is selected from adenine, guanine, uracil, cytosine and thymine; or else the monomer is a nucleotide modified in at least one of the three constituent elements; for example, the modification can occur either at the level of the bases, with modified bases such as inosine, methyl-5-desoxyuridine, desoxyuridine, dimethylamino-5-desoxyuridine, diamino-2,6-purine, bromo-5-desoxyuridine or any other modified base capable of hybridization, either at the level of the sugar, for example the replacement of at least one desoxyribose by a polyamide[11], or again at the level of the phosphate group, for example the replacement thereof by esters selected in particular from the diphosphates, alkyl- and aryl-phosphonates and phosphorothioates.

The specific binding partners of the major alternative transcript are any partner capable of binding to the major alternative transcript. By way of example, nucleic acid probes, amplification primers and any other molecule capable of binding to the major alternative transcript, may be cited.

Hybridization probe is understood to mean a nucleotide fragment comprising from 5 to 100 nucleic acid units, in particular from 10 to 35 nucleic acid units, having a hybridization specificity under defined conditions for forming a hybridization complex with the specific material of a target gene. In the present invention, the specific material of the target gene can be a nucleotide sequence contained in a messenger RNA derived from the target gene (then referred to as specific mRNA of the target gene), a nucleotide sequence contained in a complementary DNA obtained by reverse transcription of said messenger RNA (then referred to as specific cDNA of the target gene), or else a nucleotide sequence contained in a complementary RNA obtained by transcription of said cDNA as described above (then referred to as specific cRNA of the target gene). The hybridization probe can contain a marker enabling its detection.

In the sense of the present invention, an amplification primer is understood to mean a nucleotide fragment containing from 5 to 100 nucleic acid units, preferably from 15 to 30 nucleic acid units enabling the initiation of an enzymatic polymerization, such as in particular an enzymatic amplification reaction. Enzymatic amplification reaction is understood to mean a process generating multiple copies of a nucleotide fragment by the action of at least one enzyme. Such amplification reactions are well known to the person skilled in the art and the following techniques can in particular be cited:

PCR (Polymerase Chain Reaction), as described in the U.S. Pat. Nos. 4,683,195, 4,683,202 and 4,800,159, LCR (Ligase Chain Reaction), disclosed for example in the patent application EP 0 201 184, RCR (Repair Chain Reaction), described in the patent application WO 90/01069, 3SR (Self Sustained Sequence Replication) with the patent application WO 90/06995, NASBA (Nucleic Acid Sequence-Based Amplification) with the patent application WO 91/02818, and TMA (Transcription Mediated Amplification) with the U.S. Pat. No. 5,399,491.

When the enzymatic amplification is a PCR, the specific reagent includes at least 2 amplification primers, specific for a target gene, and enabling the amplification of the specific material of the target gene. The specific material of the target gene then preferably comprises a complementary DNA obtained by reverse transcription of messenger RNA derived from the target gene (then referred to as specific cDNA of the target gene) or a complementary RNA obtained by transcription of specific cDNAs of a target gene (then referred to as specific cRNA of the target gene). When the enzymatic amplification is a PCR performed after a reverse transcription reaction, it is referred to as RT-PCR.

Detection is understood to mean either a physical method or a chemical method with an intercalating dye such as SYBR® Green I or ethidium bromide, or a detection method by means of a marker. Numerous detection methods exist for the detection of nucleic acids[12,13].

Marker is understood to mean a tracer capable of generating a signal which can be detected. A non-restrictive list of these tracers includes enzymes which produce a signal detectable for example by colorimetry, fluorescence or luminescence, such as horseradish peroxidase, alkaline phosphatase, beta-galactosidase or glucose-6-phosphate dehydrogenase; chromophores such as fluorescent, luminescent or coloring compounds; groups with electron density detectable by electron microscopy or by their electrical properties such as conductivity, by the methods of amperometry or voltametry or by impedance measurements; groups detectable by optical methods such as diffraction, surface plasmon resonance, change in contact angle or by physical methods such as atomic force spectroscopy, tunnel effect, etc.; or radioactive molecules such as $^{32}P$, $^{35}S$ or $^{125}I$.

In the sense of the present invention, the hybridization probe can be a so-called detection probe. In this case, the so-called detection probe is labeled with a marker such as described above. Owing to the presence of this marker, the presence of a hybridization reaction between a given detection probe and the transcript to be detected can be detected.

The detection probe can in particular be a "molecular beacons" detection probe[14]. These "molecular beacons" become fluorescent during the hybridization. They have a structure of the stem-and-loop type and contain a fluorophore and a "quencher" group. The binding of the specific loop sequence with its complementary target nucleic acid sequence causes unwinding of the stem and the emission of a fluorescent signal on excitation at the appropriate wavelength.

The hybridization probe can also be a so-called capture probe. In this case, the so-called capture probe is immobilized or immobilizable on a solid support by any appropriate means, in other words directly or indirectly, for example by covalent bonding or adsorption. As the solid support, synthetic materials or natural materials, possibly chemically modified, in particular polysaccharides such as materials based on cellulose, for example paper, derivatives of cellulose such as cellulose acetate and nitrocellulose or dextran, polymers, copolymers, in particular on the basis of monomers of the styrene type, natural fibers such as cotton, and synthetic fibers such as nylon; inorganic materials such as silica, quartz, glasses or ceramics; latexes; magnetic particles; metal derivatives, gels, etc. can be utilized. The solid support can be in the form of a micro-titration plate, a membrane as described in the patent application WO-A-94/12670, or a particle. Several different capture probes can also be immobilized on the support, each being specific for one target transcript. In particular, a biochip on which a large number of probes can be immobilized can be utilized as the support. Biochip is understood to mean a solid support of small size where a large number of capture probes are immobilized at predetermined positions. The biochip, or DNA biochip, concept dates from the start of the 1990s. It is based on multidisciplinary technology integrating microelectronics, nucleic acid chemistry, image analysis and data processing. The operating principle is based on a foundation stone of molecular biology: the phenomenon of hybridization, in other words the pairing of two sequences of DNA and/or RNA through complementarity of the bases. The biochip method is based on the use of capture probes immobilized on a solid support which are subjected to the action of a sample of target nucleotide fragments directly or indirectly labeled with fluorochromes. The capture probes are positioned in a specific manner on the support or chip and each hybridization gives a particular piece of information, relating to the target nucleotide fragment. The information obtained is cumulative, and for example makes it possible to quantify the level of expression of a target gene/transcript or of several target genes/transcripts. After hybridization, the support or chip is washed and the labeled cDNA or cRNA/capture probe complexes are revealed by a high affinity ligand bound for example to a marker of the fluorochrome type. The fluorescence is read for example with a scanner and the analysis of the fluorescence is processed by data processing. By way of illustration, the DNA chips developed by the Affymetrix company ("Accessing Genetic Information with High-Density DNA arrays")[15,16] for molecular diagnosis can be cited. In this technology, capture probes are generally of small size, about 25 nucleotides. Other examples of biochips are given in numerous publications[17, 18, 19, 20, 21] or in the U.S. Pat. Nos. 4,981,783, 5,700,637, 5,445,934, 5,744,305 and 5,807,522. The main characteristic of the solid support must be to conserve the hybridization characteristics of the capture probes towards the target nucleotide fragments while generating minimal background noise for the detection method.

For the immobilization of the probes on the support, three major production methods are distinguished.

First of all, there is a first technique which consists in the deposition of pre-synthesized probes. The immobilization of the probes is effected by direct transfer, by means of micropipettes, micro-points or by a device of the inkjet type. This technique enables the immobilization of probes of size ranging from a few bases (5 to 10) up to relatively large sizes of 60 bases (printing) to a few hundred bases (micro-deposition):

Printing is an adaptation of the process utilized by inkjet printers. It is based on the propulsion of very small spheres of fluid (volume <1 nl) and at a rate which can reach 4000 drops/second. The printing involves no contact between the system releasing the fluid and the surface on which it is deposited.

Micro-deposition consists in immobilizing probes several tens to several hundreds of bases long on the surface of a glass slide. These probes are generally extracted from databases and are in the form of amplified and purified products. This technique makes it possible to create chips referred to as microarrays bearing about ten thousand spots, so-called recognition zones, of DNA on an area of a little less than 4 $cm^2$. However, the use of Nylon membranes, so-called "macroarrays", which bear amplified products, generally by PCR, with a diameter from 0.5 to 1 mm and whereof the maximum density is 25 spots/$cm^2$, must not be forgotten. This very flexible technique is utilized by many laboratories. In the present invention, this latter technique is regarded as being of the biochip type. However, a certain volume of sample can be deposited at the bottom of each well of a microtitration plate, as is the case in the patent applications WO-A-00/71750 and FR 00/14896, or a certain number of drops can be deposited separate from one another at the bottom of a single Petri dish, according to another patent application FR00/14691.

The second technique for immobilization of probes onto the support or chip is called in situ synthesis. This technique results in the development of short probes directly on the surface of the chip. It is based on the in situ synthesis of oligonucleotides (see in particular the patent applications WO 89/10977 and WO 90/03382), and is based on the process of oligonucleotide synthesizers. It consists in moving a reaction chamber, in which the oligonucleotide elongation reaction takes place, along the glass surface.

Finally, the third technique is called photolithography, which is a process which is behind the biochips developed by Affymetrix. This is also an in situ synthesis. Photo-lithography is derived from microprocessor technology. The surface of the chip is modified by the attachment of photolabile chemical groups capable of being activated by light. Once exposed to light, these groups are capable of reacting with the 3' end of an oligonucleotide. By protecting this surface with masks of defined shapes, it is possible to illuminate and thus activate selectively zones of the chip where it is desired to attach one or the other of the four nucleotides. The successive utilization of different masks makes it possible to alternate cycles of protection/reaction and thus to create the oligonucleotide probes on spots of about a few tens of square micrometers ($\mu m^2$). This resolution makes it possible to create up to several hundred thousand spots on an area of a few square centimeters ($cm^2$). Photolithography has advantages: massively parallel, it makes it possible to create a chip of N-mers in only 4×N cycles. All these techniques are of course utilizable with the present invention.

The biological sample utilized for the direct detection of the major alternative transcript, capable of containing the major alternative transcript as such, can consist of biological fluid or a tissue deriving from the biopsy of the tumor of the lymphatic ganglia or of metastases from the patient in question.

In order to detect the transcript from the biological sample, an extraction stage is generally necessary. It can also be detected without extraction on tissue sections by in situ hybridization techniques. The extraction is carried out by any protocols for extraction and purification of nucleic acids well known to the person skilled in the art. By way of illustration, the extraction of nucleic acids can be performed by:

a stage of lysis of the cells present in the biological sample, in order to liberate the nucleic acids contained in the patient's cells. By way of example, lysis methods such as those described in the following patent applications can be used:
WO 00/05338 on mixed magnetic and mechanical lysis,
WO 99/53304 on electrical lysis,
WO 99/15321 on mechanical lysis.
The person skilled in the art will be able to utilize other well known lysis methods, such as thermal or osmotic shock or chemical lysis with chaotropic agents such as guanidium salts (U.S. Pat. No. 5,234,809).

a purification stage, enabling the separation of the nucleic acids from the other cell components released in the lysis stage. This stage generally makes it possible to concentrate the nucleic acids, and can be adapted for the purification of RNA. For example, magnetic particles, possibly coated with oligonucleotides by adsorption or covalent bonding (on this subject see the U.S. Pat. Nos. 4,672,040 and 5,750,338) can be used, and the nucleic acids which have become attached to these magnetic particles can thus be purified by a washing stage. This nucleic acid purification stage is particularly beneficial if it is desired subsequently to amplify said nucleic acids. A particularly beneficial implementation mode of these magnetic particles is described in the patent applications: WO-A-97/45202 and WO-A-99/35500. A particularly beneficial implementation mode of these magnetic particles is described in the patent applications] of silica either in the form of a column or in the form of inert[22] or paramagnetic particles (Merck: MagPrep□ Silica, Promega: MagneSil™ Paramagnetic particles). Other very widely used methods are based on ion exchange resins in columns or in magnetic particle format (Whatman: DEAF-Magarose)[23]. Another method which is very relevant but not exclusive to the invention is that of adsorption on a metal oxide support (Xtrana company: Xtra-Bind™ matrix).

When it is desired specifically to extract the RNA from a biological sample, it is in particular possible to perform an extraction with phenol, chloroform and alcohol to remove the proteins and to precipitate the RNA with 100% ethanol. The RNA can then be spun down by centrifugation, washed and redissolved.

The biological fluid may need special treatment. The major alternative transcript may be there in solution or contained in circulating tumor cells. If the testing for the alternative transcript is directed at the fraction contained in the tumor cells, then the biological fluid will be treated beforehand so as to isolate the circulating tumor cells contained in said fluid.

Isolating the circulating tumor cells is understood to mean obtaining a cell fraction enriched in circulating tumor cells.

The treatment of the fluid to isolate the circulating tumor cells can be effected by cell sorting in a flow cytometer, by enrichment on Ficoll, by enrichment using magnetic beads coated with specific antibodies, or by any other specific enrichment method known to the person skilled in the art.

The circulating tumor cells can be isolated by means of a technique of cell separation on Ficoll combined with depletion of the blood cells utilizing anti-CD45 antibodies coupled to magnetic beads (Dynal Biotech ASA, Norway).

The direct detection of the major alternative transcript can then be performed directly from circulating tumor cells isolated from the biological fluid. For example, the circulating tumor cells deposited on a slide by cyto spin can be placed in contact with a probe specific for the major alternative transcript so as to effect an in situ hybridization.

One example of an indirect method consists in translating the RNA extracted from samples into proteins in vitro, for example by means of expression systems such as *E. coli*, then detecting the specific translation product of the alternative RNA by an immunological test such as "sandwich" tests, for example ELISA, or competition tests. These methods are widely known to the person skilled in the art and utilize in particular monoclonal and/or polyclonal antibodies as the specific binding partner of the peptide translated from RNA.

The method of the invention can be implemented by stages consisting in:
  i) determining the quantity of major alternative transcript in the biological sample,
  ii) comparing the quantity of major alternative transcript in the biological sample with a predetermined threshold value, selected depending on the type of assay utilized and representative of the detection limit of the pathology and
  iii) establishing the diagnosis.

The quantification of the concentration of major alternative transcript can be carried out by any method known to the person skilled in the art for quantifying a marker in a biological sample, such as by utilizing a hybridization test, as described above.

Also as stated above, it is known that in general the results of nucleic acid detection tests depend to a large extent on the characteristics of the binding partners utilized, so that it is not possible to give precise threshold values, and that threshold values adapted to each binding partner utilized can be determined in each case by simple routine experiments.

The diagnostic method of the invention can be improved by also including a supplementary stage of detecting at least one other transcript of the KLK8 gene, which constitutes a particular implementation mode of the invention.

Other transcript of the KLK8 gene is understood to mean:
  other alternative transcripts of the KLK8 gene, called minor transcripts, such as those already known as NT2, NT3 and NT4, as well as new transcripts discovered by the Applicants, called NT5 and NT6,
  the transcript encoding kallikrein KLK8 also called NT1.

The new transcripts NT5 and NT6, of sequences SEQ ID No7 and SEQ ID No8 respectively are novel and constitute another subject of the invention.

The diagnostic method of the invention including a supplementary stage of detection of another alternative transcript of the KLK8 gene can be implemented the stages consisting in:
  i) determining the quantity of major alternative transcript of the KLK8 gene and of other, possibly alternative, transcript of the KLK8 gene in the same biological sample, and
  ii) comparing the quantity obtained with a predetermined threshold value, selected depending on the type of assay utilized and representative of the detection limit of the pathology and
  iii) establishing the diagnosis.

The determination of the quantity of major alternative transcript of KLK8 and of other, possibly alternative, transcript of the same KLK8 gene can be carried out consecutively or simultaneously, by the methods customarily known to the person skilled in the art.

Same biological sample is understood to mean a sample of the same nature taken from the same subject, namely either two fractions from the same sampling, or two samples derived from two different samplings but which must be of the same nature, for example of cancerous tissue. Two samples from the same sampling are preferably utilized.

The diagnostic method of the invention can also include a supplementary stage of detecting at least one transcript of a gene of another kallikrein, which constitutes another implementation mode of the invention.

The method thus detects at least one transcript of a gene of another kallikrein, as well as:
  (a) either at least one major alternative transcript of the KLK8 gene or
  (b) at least one major alternative transcript of the KLK8 gene and at least one minor, possibly alternative, transcript of the KLK8 gene.

This method can be implemented by stages consisting in:
  i) determining the quantity of major alternative transcript of the KLK8 gene, and possibly of the other, possibly alternative, transcript of the KLK8 gene, in the biological sample Q1,
  ii) determining the quantity of the transcript of the other kallikrein gene in the same sample Q2,
  iii) calculating the ratio Q1/Q2 or Q2/Q1, iv) comparing said ratio with a predetermined threshold value, selected depending on the type of assay utilized and representative of the detection limit of the pathology and v) establishing the diagnosis.

By way of example of another gene of kallikrein appropriate for the purposes of the invention, the genes of kallikreins expressed in the lung, such as KLK5, KLK6, KLK7, KLK10, KLK11, KLK13 and KLK14 can be cited. These genes of kallikreins have been widely described in the literature so that they are known to the person skilled in the art. The genes of kallikreins KLK5, KLK11 and KLK13 are preferred, KLK11 being particularly preferred.

As stated above, the determination of the quantity of the transcripts of different nature can be carried out consecutively or simultaneously, by the methods customarily known to the person skilled in the art as described above, and same biological sample is understood to mean a sample of the same nature taken from the same subject.

Beside the detection of the major alternative transcript of the KLK8 gene, the diagnostic method of the invention can also include the stage of detecting at least one transcript of another gene expressed in the lung, understood to be different from a gene coding for a kallikrein.

As examples of other genes expressed in the lung, the genes encoding the desmosomal cadherins, such as desmocollin 2 or Dsc2 and desmoglein 2 or Dsg2, can be cited.

The method which further includes the stage of detecting at least one transcript of another gene expressed in the lung can be implemented by stages consisting in:

i) determining the quantity of major alternative transcript of the KLK8 gene in the biological sample Q1, ii) determining the quantity of the transcript of the other gene expressed in the lung in the same biological sample Q4, iii) calculating the ratio Q1/Q4 or Q2/Q4, iv) comparing said ratio with a predetermined threshold value, selected depending on the type of assay utilized and representative of the detection limit of the pathology and v) establishing the diagnosis.

As stated above, the determination of the quantity of the transcripts of different nature can be carried out consecutively or simultaneously, by the methods customarily known to the person skilled in the art as described above, and same biological sample is understood to mean a sample of the same nature taken from the same subject.

In each implementation mode of the invention, the last stage consists in establishing the diagnosis.

Diagnosis is understood to mean both diagnosis in the broad sense of the term, namely both early diagnosis and screening, therapeutic monitoring, prognosis and the diagnosis of relapses.

The type of diagnosis will depend on the nature of the biological sample in which the method of the invention is carried out. Thus, biological fluids will preferably be utilized in the context of early diagnosis, screening, diagnosis of relapses and possibly therapeutic monitoring. In the case of solid samples, such as cancerous tissue, lymphatic ganglia or metastases, the carcinoma is already known to be present. The method of the invention will therefore be useful in the context of prognosis and possibly of therapeutic monitoring.

The method of the invention is particularly appropriate in survival prognostication in patients suffering from bronchopulmonary carcinoma. In fact, the Applicants have shown that a high level of major alternative transcript of the KLK8 gene, in particular of NT3 and NT4, is an adverse prognostic factor in cancer and in particular in NSCBC.

Thus, another subject consists in the utilization of the diagnostic method of the invention in the survival prognostication of patients suffering from bronchopulmonary carcinoma.

As before, the prognostication is improved by inclusion of one of the following stages:

stage of detecting at least one other, possibly alternative, transcript of the KLK8 gene, stage of detecting at least one transcript of another gene of kallikrein, preferably KLK5, KLK11 and KLK13, KLK11 being particularly preferred, possibly in combination with the detection of at least one other alternative transcript of the KLK8 gene, stage of detecting at least one transcript of another gene expressed in the lung.

For the implementation of the diagnostic method of the invention, another subject of the invention is a diagnostic kit containing the tools necessary for the detection of the major alternative transcripts of the KLK8 gene.

As non-limiting examples of tools necessary for the detection of the major alternative transcripts of the KLK8 gene, the binding partners of said major transcripts, such as the hybridization and detection probes can be cited.

The invention also relates to the utilization of at least one of the major alternative transcripts of the KLK8 gene encoding kallikrein 8 in the production of an agent utilized in a detection method in the context of bronchopulmonary carcinoma, in particular of non-small cell bronchial carcinoma, the method being characterized in that it consists in contacting said at least one major alternative transcript of the KLK8 gene with a biological sample derived from a patient suspected to be suffering from said bronchopulmonary carcinoma.

Figure 2:
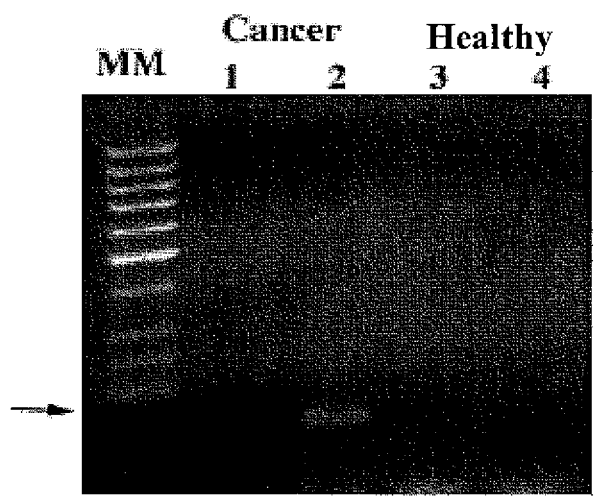
FIG. 2 is a photograph of an electrophoresis gel showing the presence of transcript NT4 in the blood of a patient suffering from carcinoma, the left-hand track corresponding to the molecular weight marker track (MM).

The invention will be better understood with the aid of the following examples given by way of illustration and non-restrictively, and with the aid of the appended FIGS. 1 and 2.

EXAMPLE 1

Demonstration of the Major Pulmonary Transcripts of the Gene KLK8 and Novel Transcripts Total RNA was extracted from cancerous tissues of patients suffering from adenocarcinoma or epidermoid carcinoma utilizing the "RNAeasy Midi kit" system (Qiagen S.A., Courtabœuf, France) according to the manufacturer's recommendations. The total RNA was retrotranscribed to cDNA by means of PowerScript Reverse Transcriptase (BD Biosciences Clontech, Palo Alto, Calif.).

For each sample, a reverse transcription reaction was performed at 42° C. for one hour in a final volume of 20 µl. The reaction medium was made up of 2 µg of total RNA, 5 µM of aspecific decameric oligonucleotides (Random decamers RETROscript, Ambion, Cambridgeshire), and dNTP each at the concentration of 1 mM, 20 U of RNase inhibitor (Roche Diagnostics, Meylan), 1×—concentrated reaction buffer and one unit of Power Script Reverse Transcriptase (BD Biosciences Clontech, Palo Alto, Calif.).

The cDNA were amplified by PCR. The reaction mixture of 25 µl contained: 50 ng of total RNA retrotranscript, 1 unit of FastStart Taq DNA (Polymerase Roche Diagnostics, Meylan), 1×—concentrated reaction buffer (50 mM Tris-HCl pH 8.3, 10 mM KCl, 5 mM (NH4)$_2$SO$_4$, 2 mM MgCl$_2$), dNTP at the concentration of 0.3 mM and 0.2 µM of the specific primers.

These primers were selected on either side of the sequence encoding kallikrein KLK8 (NT1) and contained a restriction enzyme cleavage site (Not 1 or EcoR V). These primers were:

```
K8Not_for:
                                        (SEQ ID N° 1)
TGG AGG GCG GCC GCA TGG GAC GCC CCC GAC
and K8Eco_rev:
                                        (SEQ ID N° 2)
TCC TAG ATA TCG CCC TTG CTG CCT ATG.
```

The PCR reactions were performed in a temperature gradient thermocycler (Master cycler Gradient, Eppendorf). The amplification conditions were as follows: a denaturation cycle of 5 min at 95° C. followed by 45 cycles comprising a denaturation stage at 95° C. for 20 s, a hybridization stage at 56° C. for 20 s and an elongation stage at 72° C. for 1.30 minutes. The reaction was terminated by a supplementary elongation cycle of 1.30 mins at 72° C.

Ten microliters from the reaction were deposited on 0.8% agarose gel containing 0.5 µg/ml of ethidium bromide. The products were separated by electrophoresis and viewed under W. The size marker utilized (Gene Ruler DNA Ladder mix) was supplied by the firm MBI-Fermentas.

The photograph of the electrophoresis gel is given in FIG. 1 which shows the various transcripts derived from the pulmonary expression of the KLK8 gene and the characterization of major transcripts of NT3 and NT4. It should be noted that these transcripts have been identified by nucleotide sequencing (see example 2) as being the transcripts already described under the name of Neuropsin type 1 to 4 (NT1 to NT4), the two new transcripts having been identified and named NT5 and NT6.

EXAMPLE 2

Structural Characterization of the Pulmonary Transcripts of the Gene KLK8 and Design of Specific Primers The PCR products obtained in Example 1 were cloned in the vector pcDNA5-FRT-V5-His TOPO (Invitrogen, Cergy Pontoise) according to the manufacturer's recommendations. The preparation of plasmid DNA was effected from various clones utilizing the "Qiaprep MiniPrep" system (Qiagen S.A, Courtaboeuf). The purified plasmid DNA was then quantified by spectrophotometry at 260 nm, then sequenced in both directions by means of the primer pair T7 and pCR 3.1 (BGH_rev). The sequences obtained, given below, were compared with the sequences contained in the databases. The structure of the cloned transcripts, given in Table 1, was determined by alignment with the sequence of the KLK8 gene using the CLUSTAL W software.

Sequence of pulmonary cDNA YC170310.03 identical to the transcript NT1 (NM_007196).: SEQ ID No3

Sequence of pulmonary cDNA YC140710.03 identical to the transcript NT2 (NM_144505).: SEQ ID No4

Sequence of pulmonary cDNA YC090310.03 identical to the transcript NT3 (NM_144506). SEQ ID No5

Sequence of pulmonary cDNA YC100310.03 identical to the transcript NT4 (NM_144507).: SEQ ID No6

Sequence of pulmonary cDNA YC210710.03 corresponding to a novel transcript (NT5).: SEQ ID No7

Sequence of pulmonary cDNA YC050710.03 corresponding to a novel transcript (NT6).: SEQ ID No8

TABLE 1

| Pulmonary transcript | Generic name | Structure |
|---|---|---|
| YC170310.03 | NT1 | EX1 + EX2 + EX3 + E4 + EX5 + EX6 |
| YC140710.03 | NT2 | EX1 + EX2 + EX3 ALT + EX4 + EX5 + EX6 |
| YC090310.03 | NT3 | EX1 + EX2 + EX5 + EX6 |
| YC100310.03 | NT4 | EX1 + EX2 + EX6 |
| YC210710.03 | NT5 | EX1 + EX2 + EX4 + EX5 + EX6 |
| YC050710.03 | NT6 | EX1 + EX2 + EX3 + EX5 + EX6 |

EX = exon; ALT = alternative exon

As is shown by Table 1, the pulmonary transcripts differ from one another only by different combinations of identical exons. It is therefore not possible to target them individually by exploiting novel sequences (except for NT2 which possesses an additional sequence at in 5' of the exon 2). Knowledge of the pulmonary transcriptome of the gene KLK8 makes it possible to determine for each transcript the combination of exons distinguishing it from the other transcripts present in this tissue, as shown in Table 2.

TABLE 2

| Pulmonary transcript | Generic name | Distinctive combination at the pulmonary level |
|---|---|---|
| YC170310.03 | NT1 | EX2-EX3 + EX4-EX5 |
| YC140710.03 | NT2 | EX2-EX3 ALT |
| YC090310.03 | NT3 | EX2-EX5 |
| YC100310.03 | NT4 | EX2-EX6 |
| YC210710.03 | NT5 | EX2-EX4 |
| YC050710.03 | NT6 | EX3-EX5 |

The utilization in the hybridization or detection probes of the junction sequences of the exons present in these combinations is therefore the only means of specifically and individually targeting the pulmonary transcripts. This was exploited to generate the amplification primer conferring specificity of quantification of the major transcripts NT3 and NT4 in this organ (see Table 3).

TABLE 3

| Transcript targeted | Location of the primer | Name of the specific sense primer and sequence (SEQ ID N°) |
|---|---|---|
| NT3 | Junction EX2-EX5 | NT3_for: GGA GCC TGG GCA GAG AAT (SEQ ID N° 9) |
| NT4 | Junction EX2-EX6 | NT4-2/6: TGG GCA GGG CGA TTC T (SEQ ID N° 10) |

EXAMPLE 3

Quantification of the Transcripts NT3 and NT4 in the Tumor Tissues from Patients Suffering from Pulmonary Carcinoma The transcripts NT3 and NT4 were assayed by quantitative real time PCR in the presence of the intercalating fluorophore "SYBR Green" in an iCycler iQ Detection System thermocycler (Biorad, Marnes la Coquette). Each assay included two measurements for quantification of the cDNA deriving from pulmonary tumor samples, two measurements of controls with no DNA and a calibration curve constructed using various dilutions of standard plasmid DNA isolated from the clones YC090310.03 (NT3) and YC100310.03 (NT4) (see Example 2). The values found for each sample were normalized with that determined during the quantification of transcripts encoding the ribosomal subunit 18S. In this latter case, the calibration curves were created from different dilutions of a sequence from this gene (853 bp) amplified by conventional PCR and purified directly using the Macherey Nagel kit according to the manufacturer's recommendations. The oligonucleotides utilized for obtaining this sequence were:

```
oligo 18S_for:
                                  (SEQ ID N° 11)
CTA CCA CAT CCA AGG AAG GCA GCA
and oligo 18S_rev:
                                  (SEQ ID N° 12)
GCT ATC AAT CTG TCA ATC CTG TCC.
```

The reaction mixture for the quantitative amplification of NT3 and NT4 contained: 100 ng of total RNA retro-transcript (see Example 1), 1 unit of FastStart Taq DNA Polymerase, SYBR Green (Roche Diagnostics, Meylan) 0.2×—concentrated, 1×—concentrated reaction buffer (50 mM Tris-HCl pH 8.3, 10 mM KCl, 5 mM $(NH_4)_2SO_4$, 2 mM $MgCl_2$), dNTP each at the concentration of 0.2 mM and 0.2 µM of each sense (Table III, Example 2) and antisense oligonucleotide primer of the transcript studied. The antisense primers of the transcripts NT3 and NT4 were respectively: the primer NT3_rev (CCT CCA GAA TCG CCC T—SEQ ID No13) hybridizing with the junction sequence of the exons 5 and 6, and the primer NT4_rev (CAG TCC AGG TAG CGG CAG—SEQ ID No14) the targeted sequence whereof is situated in the exon 6.

The measurements for quantification of the housekeeping gene encoding the ribosomal subunit 18S were performed in the following reaction medium: 0.5 ng of total RNA retro-transcript, 1 unit of FastStart Taq DNA Polymerase, SYBR Green 0.2× concentrated, 1×—concentrated reaction buffer (50 mM Tris-HCl pH 8.3, 10 mM KCl, 5 mM $(NH_4)_2SO_4$, 2 mM $MgCl_2$) to which had been added 2 mM $MgCl_2$, dNTP each at the concentration of 0.2 mM and 0.56 µM of each sense (CGC GGT TCT ATT TTG TTG GTT TT—SEQ ID No15) and antisense (TTC GCT CTG GTC CGT CTT GC—SEQ ID No16) primer.

The amplification conditions for the quantitative PCR of the various transcripts are shown in Table 4.

TABLE 4

| Number of cycle(s) | Stage | Duration | Temperature | Transcripts |
|---|---|---|---|---|
| 1 cycle | Denaturation | 5 min | 95° C. | NT3, NT4, 18S |
| 50 cycles | Denaturation | 10 s | 95° C. | NT3, NT4, 18S |
| | Hybridization | 10 s | 59° C. | NT3 |
| | | 10 s | 61° C. | NT4 |
| | | 10 s | 65° C. | 18S |
| | Elongation | 15 s | 72° C. | NT3, NT4 |
| | | 20 s | 72° C. | 18S |
| | Acquisition of fluorescence | 15 s | 81° C. | NT3, NT4 |
| | | 15 s | 84° C. | 18S |

The quantifications were performed on samples of tumor tissue taken from surgically ablated pieces from patients operated for bronchopulmonary carcinoma between January 2002 and June 2004. The cohort studies comprised 60 patients whose age varied from 45 to 83 years with a median age of 65 years (see Table 5).

TABLE 5

| Tumor type | Number of patients |
|---|---|
| Adenocarcinoma | 33 |
| Epidermoid carcinomas | 16 |
| Large cell carcinoma | 5 |
| Muco-epidermoid carcinoma | 1 |
| Neuro-endocrine carcinoma | 1 |
| Carcinoid tumor | 4 |

Thirty-eight patients had a stage 1 or 2 carcinoma according to the pTNM classification[24], and 24 patients a stage 3 or 4 carcinoma. The survival analysis was carried out by collecting information relating to their state of health in January 2006. We recorded 26 deaths during the study period.

For the normalized values of NT3 and NT4 expressed in arbitrary units (AU), we determined, by means of a $\chi^2$ test, a threshold value making it possible to best predict the overall survival of the population. The threshold value is 50 AU for NT3 ($\chi^2=7.54$; P=0.006) and 1000 AU for NT4 ($\chi^2=7.54$; P=0.006). These values, representing the $45^{th}$ and $46^{th}$ percentiles, were utilized for the subsequent analyses.

The patients were classed into two groups: one group corresponds to the individuals exhibiting an expression level lower than the threshold value determined (weak expression; referred to as weak NT3 or NT4), and one group having a higher expression level (strong expression; referred to as weak NT3 or NT3). For each group, a survival curve was constructed by the Kaplan-Meier method and the significance of the differences between the curves was evaluated by the log rank test. The impact of the expression of the transcripts (comparison of strong expression versus weak expression) on the overall survival of the patients was evaluated by the HR (relative risk of death) which was calculated using the Cox model (Cox proportional hazards regression model). The analysis was carried out univariately. It was also carried out after adjustment for the tumor stage (which makes it possible to eliminate the variable "stage") since this variable is strongly linked with the survival of the patients (then referred to as adjusted strong NT3 or NT4).

The results are shown in Table 6.

TABLE 6

| Variables | Kaplan-Meier and log rank test P | Cox model HR | Cox model 95% CI | Cox model P |
|---|---|---|---|---|
| strong NT3 vs weak NT3 | 0.015 | 2.860 | 1.147-7.128 | 0.0241 |
| stages 3 + 4 vs stages 1 + 2 | NC | 3.609 | 1.583-8.229 | 0.0023 |
| adjusted strong NT3 vs adjusted weak NT3 | | 2.300 | 0.911-5.804 | 0.0779 |
| strong NT4 vs weak NT4 | 0.005 | 3.608 | 1.448-8.994 | 0.0059 |
| stages 3 + 4 vs stages 1 + 2 | NC | 4.253 | 1.861-9.719 | 0.0006 |
| adjusted strong NT4 vs stages 1 + 2 | | 3.712 | 1.478-9.323 | 0.0052 |

NC: not calculated and CI: confidence interval, vs = versus

The Kaplan-Meier survival curves display significant differences in survival (log rank test, Table 6) between the patients strongly expressing NT3 or NT4 (strong NT3 or NT4) and the patients weakly expressing these transcripts (P calculated with regard to weak NT3 or NT4).

The Cox model makes it possible to conclude that patients strongly expressing the transcripts have significantly lower survival than the other patients. In fact, the Cox analysis shows that the increase in the risk of death linked to strong expression of NT3 (increased by a factor of 2.860; HR, Table 6) or of NT4 (increased by a factor of 3.608; HR, Table 6) is statistically significant. The expression levels of these transcripts thus constitute prognostic indicators of patient survival for carcinoma of the lung.

After adjustment for the tumor stage (adjusted strong NT3 or NT4), it is found that the increase in the risk of death linked with "strong NT3" loses statistical significance (P=0.0779). This indicates that the two variables (expression of NT3 and tumor stage) appear to be linked in this study.

Nonetheless, the strong tendency of "adjusted strong NT3" to significance suggests that the two variables could turn out to be independent in a more robust study comprising a greater number of events.

The situation is different for the variable "strong NT4" since adjustment for the tumor stage does not change the statistical significance of the increase in the risk of death. This result proves that the variable NT4 is a prognostic indicator independent of the tumor stage.

EXAMPLE 4

Assay of the Transcripts NT3 or NT4 in Combination with the Assay of Transcripts of Other Genes of the Kallikreins The strategy for assay of transcripts of other genes of kallikreins expressed in the lung (KLK5, KLK6, KLK7, KLK10, KLK11, KLK13 and KLK14) is identical to that described in Example 3. In summary, the quantity of products derived from the amplification of the cDNA and the controls was determined after each cycle by means of the incorporation of SYBR green. Standard curves were created on the basis of plasmid DNA deriving from clones of cDNA of the different genes. The values found for each patient and each gene were normalized with the values for ribosomal 18S and expressed in arbitrary units. The reaction conditions were identical to those described for NT3 and NT4 (Example 3). The PCR primers utilized are described in Table 7.

TABLE 7

| Name | Sequences | genes | orientations | SEQ ID N° |
|---|---|---|---|---|
| K5.398_for | GCC ACT ACT CCC TGT CAC CA | KLK5 | Sense | 17 |
| K5.682_rev | GCA TCC TCG CAC CTT TTC TG | | antisense | 18 |
| 256.K6_for | TGA TGG TGG TGC TGA GT | KLK6 | Sense | 19 |
| 393.K6_rev | ACA GTG GAT GGA TAA GGA C | | antisense | 20 |
| 547.K7_for | GAG CCC AGA TGT GAC CTT | KLK7 | Sense | 21 |
| 615.K7_rev | TCC TTG TAA ACC TTC GTG C | | antisense | 22 |
| 2K10.210_for | GGA CCC CGA AGC CTA TG | KLK10 | Sense | 23 |
| 2K10.442_rev | CCT GAG CCC TGG TGG TA | | antisense | 24 |
| K11_for2 | CAG GAT CAT CAA GGG GTT CG | KLK11 | Sense | 25 |
| K11_rev2 | CAT TGC GGT GGT CTT TGT TG | | antisense | 26 |
| 576.K13_for | GTG CCA ACA TCC AAC TTC G | KLK13 | Sense | 27 |
| 672.K13_rev | CCC TCA CAG GAG TCT TTG C | | antisense | 28 |
| 448.K14_for | TGG GTC ATC ACT GCT GCT C | KLK14 | Sense | 29 |
| 500.K14_rev | CTC CTC AGG TTG TGC TTG C | | antisense | 30 |

TABLE 8

| Number of cycle(s) | Stage | Duration | Temperature | Transcripts |
|---|---|---|---|---|
| 1 cycle | Denaturation | 5 min | 95° C. | all |
| 50 cycles | Denaturation | 10 s | 95° C. | all |
| | Hybridization | 15 s | 57° C. | KLK10 and 11 |
| | | 10 s | 59° C. | KLK14 |
| | | 10 s | 60° C. | KLK7 |
| | | 15 s | 65° C. | KLK5, 6 |
| | | 15 s | 68° C. | KLK13 |
| | Elongation | 15 s | 72° C. | KLK10 and 14 |
| | | 20 s | 72° C. | KLK5, 6, 7, 11 and 13 |
| | Acquisition of fluorescence | 15 s | 80° C. | KLK7 |
| | | 15 s | 81° C. | KLK14 |
| | | 15 s | 84° C. | KLK6, 11, 13 |
| | | 15 s | 86° C. | KLK5, 10 |

The cohorts utilized for the assay of the transcripts of the various genes derive from the population studied in Example 3. The distribution of the tumor histological types within the cohorts studied is given in Table 9.

TABLE 9

| Tumor type | KLK5, 7 | KLK6 | KLK10, 11, 13 | KLK14 |
|---|---|---|---|---|
| Adenocarcinoma | 29 | 33 | 28 | 33 |
| Epidermoid carcinomas | 16 | 16 | 16 | 15 |
| Large cell carcinoma | 4 | 5 | 3 | 5 |
| Muco-epidermoid carcinoma | 1 | 1 | 1 | 1 |
| Neuro-endocrine carcinoma | 1 | 1 | 1 | 1 |
| Carcinoid tumor | 3 | 4 | 1 | 4 |
| Total number | 54 | 60 | 50 | 59 |

For each patient, the expression level of the different transcripts was determined and was then used to calculate a ratio with NT3 or with NT4 (Table 10 for NT3 and Table 11 for NT4). For each ratio, we then determined a threshold value making it possible to best predict the overall survival of the population by means of the method described in Example 3.

TABLE 10

| Variable | Threshold | $\chi^2$ | P | percentile | deaths |
|---|---|---|---|---|---|
| NT3/KLK5 | 0.05 | 5.54 | 0.019 | 46 | 26 |
| NT3/KLK6 | 0.005 | 5.54 | 0.019 | 42 | 26 |
| NT3/KLK7 | 0.001 | 7.54 | 0.006 | 37 | 26 |
| NT3/KLK10 | 0.01 | 10.66 | 0.001 | 36 | 24 |
| NT3/KLK11 | 0.0015 | 8.17 | 0.004 | 40 | 24 |
| NT3/KLK13 | 0.008 | 8.17 | 0.004 | 40 | 24 |
| NT3/KLK14 | 0.10 | 6.00 | 0.014 | 53 | 24 |

TABLE 11

| Variable | Threshold | $\chi^2$ | P | percentile | deaths |
|---|---|---|---|---|---|
| NT4/KLK5 | 2 | 3.84 | 0.049 | 53 | 26 |
| NT4/KLK6 | 2 | 3.84 | 0.049 | 43 | 26 |
| NT4/KLK7 | 0.1 | 7.50 | 0.006 | 39 | 26 |
| NT4/KLK10 | 0.4 | 5.99 | 0.014 | 42 | 24 |
| NT4/KLK11 | 0.1 | 10.66 | 0.001 | 44 | 24 |
| NT4/KLK13 | 0.7 | 8.17 | 0.004 | 46 | 24 |
| NT4/KLK14 | 0.5 | 5.99 | 0.014 | 52 | 24 |

As in Example 3, the patients were classed into two groups: one group corresponds to the individuals exhibiting an expression level lower than the threshold value determined (weak expression), and one group having a higher expression level (strong expression). For each group, a survival curve was constructed by the Kaplan-Meier method and the significance of the differences between the curves was evaluated by the log rank test. The relative risk of death (HR) was calculated using the Cox model (Cox proportional hazards regression model). The analysis was carried out after adjustment for the tumor stage since this variable is strongly linked with the survival of the patients.

The results for NT3 are given in Table 12.

TABLE 12

| Variables | Kaplan-Meier and log rank test P | Cox model HR | 95% CI | P |
|---|---|---|---|---|
| strong NT3/KLK5 vs weak NT3/KLK5 | 0.0214 | NC | NC | NC |
| stages 3 + 4 vs stages 1 + 2 | NC | 3.549 | 1.553-8.110 | 0.0027 |
| adjusted strong NT3/KLK5 vs adjusted weak NT3/KLK5 | | 2.570 | 1.064-6.211 | 0.0360 |

TABLE 12-continued

| Variables | Kaplan-Meier and log rank test P | Cox model HR | 95% CI | P |
|---|---|---|---|---|
| strong NT3/KLK6 vs weak NT3/KLK6 | 0.0378 | NC | NC | NC |
| stages 3 + 4 vs stages 1 + 2 | NC | 3.662 | 1.609-8.335 | 0.0020 |
| adjusted strong NT3/KLK6 weak vs NT3/KLK6 | | 2.245 | 0.891-5.657 | 0.0864 |
| strong NT3/KLK7 vs weak NT3/KLK7 | 0.0564 | NC | NC | NC |
| stages 3 + 4 vs stages 1 + 2 | NC | 3.572 | 1.564-8.158 | 0.0025 |
| adjusted strong NT3/KLK7 vs adjusted weak NT3/KLK7 | | 2.337 | 0.925-5.906 | 0.0727 |
| strong NT3/KLK10 vs weak NT3/KLK10 | 0.0126 | NC | NC | NC |
| stages 3 + 4 vs stages 1 + 2 | NC | 3.476 | 1.517-7.966 | 0.0032 |
| adjusted strong NT3/KLK10 vs weak NT3/KLK10 | | 2.439 | 0.962-6.182 | 0.0602 |
| strong NT3/KLK11 vs weak NT3/KLK11 | 0.0085 | NC | NC | NC |
| stages 3 + 4 vs stage 1 + 2 | NC | 3.958 | 1.743-8.990 | 0.0010 |
| adjusted strong NT3/KLK11 vs adjusted weak NT3/KLK11 | | 2.969 | 1.244-7.086 | 0.0142 |
| strong NT3/KLK13 vs weak NT3/KLK13 | 0.0041 | NC | NC | NC |
| stages 3 + 4 vs stages 1 + 2 | NC | 3.473 | 1.520-7.935 | 0.0031 |
| adjusted strong NT3/KLK13 vs adjusted weak NT3/KLK13 | | 2.923 | 1.160-7.364 | 0.0229 |
| strong NT3/KLK14 vs weak NT3/KLK14 | 0.0205 | NC | NC | NC |
| stages 3 + 4 vs stages 1 + 2 | NC | 3.669 | 1.604-8.392 | 0.0021 |
| adjusted strong NT3/KLK14 vs adjusted weak NT3/KLK14 | | 1.823 | 0.814-4.082 | 0.1444 |

NC: not calculated and CI: confidence interval

This study establishes that patients having NT3/KLKx ratios greater than the threshold value exhibit a significantly decreased survival rate compared to those in whom the value of the ratio is lower than the threshold value (with the exception of NT3/KLK7; log rank test).

The results of the Cox test show that the ratios NT3/KLK5, NT3/KLK11 and NT3/KLK13 are prognostic indicators independent of the tumor stage (P<0.05 for the adjusted variable). The creation of a ratio of the expression of NT3 to the expression of the genes KLK5, KLK11 and KLK13 thus improves the predictive power of NT3 since this variable alone is not totally independent of the variable "tumor stage" in the population studied (see Example 3).

The results for NT4 are given in Table 13.

TABLE 13

| Variables | Kaplan-Meier and log rank test P | Cox model HR | 95% CI | P |
|---|---|---|---|---|
| strong NT4/KLK5 vs weak NT4/KLK5 | 0.0054 | NC | NC | NC |
| stages 3 + 4 vs stage 1 + 2 | NC | 3.703 | 1.621-8.456 | 0.0019 |
| adjusted strong NT4/KLK5 vs adjusted weak NT4/KLK5 | | 3.131 | 1.349-7.270 | 0.0079 |
| strong NT4/KLK6 vs weak NT4/KLK6 | 0.0629 | NC | NC | NC |
| stages 3 + 4 vs stage 1 + 2 | NC | 3.802 | 1.678-8.617 | 0.0014 |
| adjusted strong NT4/KLK6 vs weak NT4/KLK6 | | 2.073 | 0.864-4.974 | 0.1024 |
| strong NT4/KLK7 vs weak NT4/KLK7 | 0.0010 | NC | NC | NC |

TABLE 13-continued

| Variables | Kaplan-Meier and log rank test P | Cox model HR | Cox model 95% CI | Cox model P |
|---|---|---|---|---|
| stages 3 + 4 vs stages 1 + 2 | NC | 4.468 | 1.948-10.245 | 0.0004 |
| adjusted strong NT4/KLK7 vs adjusted weak NT4/KLK7 | | 3.657 | 1.458-9.178 | 0.0057 |
| strong NT4/KLK10 vs weak NT4/KLK10 | 0.0012 | NC | NC | NC |
| stage 3 + 4 vs stages 1 + 2 | NC | 3.807 | 1.672-8.667 | 0.0014 |
| adjusted strong NT4/KLK10 vs adjusted weak NT4/KLK10 | | 3.802 | 1.521-9.503 | 0.0043 |
| strong NT4/KLK11 vs weak NT4/KLK11 | 0.0001 | NC | NC | NC |
| stages 3 + 4 vs stages 1 + 2 | NC | 4.437 | 1.917-10.269 | 0.0005 |
| adjusted strong NT4/KLK11 vs adjusted weak NT4/KLK11 | | 6.362 | 2.330-17.366 | 0.0003 |
| strong NT4/KLK13 vs weak NT4/KLK13 | 0.0018 | NC | NC | NC |
| stages 3 + 4 vs stage 1 + 2 | NC | 3.789 | 1.669-8606 | 0.0015 |
| adjusted strong NT4/KLK13 vs adjusted weak NT4/KLK13 | | 3.255 | 1.410-7.510 | 0.0057 |
| strong NT4/KLK14 vs weak NT4/KLK14 | 0.0018 | NC | NC | NC |
| stages 3 + 4 vs stages 1 + 2 | NC | 3.718 | 1.634-8.459 | 0.0017 |
| adjusted strong NT4/KLK14 vs adjusted weak NT4/KLK14 | | 2.821 | 1.217-6.537 | 0.0156 |

NC: not calculated and CI: confidence interval

As is shown by Table 13, patients having NT4/KLKx ratios greater than the threshold value exhibit a significantly decreased survival rate compared to those in whom the value of the ratio is lower than the threshold value (with the exception of NT3/KLK6; log rank test). The results of the Cox test show that apart from the NT3/KLK6 ratio, all the other ratios constitute prognostic indicators independent of the tumor stage (P<0.05 for the adjusted variable). In this study, the NT4/KLK11 ratio appears particularly effective since the relative risk of death calculated with this variable is greater than that obtained with the tumor stage.

EXAMPLE 5

Quantification of the Transcript NT3 in Combination with Other Transcripts of the Gene KLK8 (NT1, NT2, NT5 and NT6), Possibly in Combination with Other Transcripts of Kallikrein In the previous examples, the transcripts NT3 and NT4 were assayed separately through the use of discriminating PCR primers. This example aims to evaluate the prognostic value of these transcripts when they are assayed by means of non-discriminating PCR primers. We used oligonucleotides targeting the exons 5 and 6 and thus enabling the overall quantification of the transcripts NT1, NT2, NT3, NT5 and NT6. The variable measured was named "KLK8". The sequences of these primers are:

```
719.K8_for:
                              (SEQ ID N° 31)
CCA GAA GAA GTG TGA GGA TG
and 890.K8_rev:
                              (SEQ ID N° 32)
GGT ATA GAC GCC AGG TTT G.
```

The reaction mixture utilized was identical to that of Example 3 since the amplification conditions were: 1 cycle of 5 min at 95° C. then 50 cycles comprising a denaturation stage of 20 s at 95° C., a hybridization stage of 20 s at 60° C., an elongation stage of 20 s at 72° C. and a fluorescence acquisition stage of 15 s at 84° C. The procedure was identical to that of the previous examples, namely: (1) quantification of the variable by means of a standard curve, (2) normalization with the expression level or ribosomal 18 S RNA, (3) expression in the form of an arbitrary value, possibly in comparison to the expression of another gene, (4) definition of a threshold value by chi$^2$ test (Table 14), (5) binarization of the population (strong expression>threshold; weak expression<threshold), (6) statistical tests (Table 15).

The cohorts studied were the same as in Example 3 for the variable "KLK8", and as in Example 4 for the expression in the form of a ratio to other kallikrein genes.

TABLE 14

| Variable | Threshold | $\chi^2$ | P | percentile | deaths |
|---|---|---|---|---|---|
| KLK8 | 250 | 7.54 | 0.006 | 42 | 26 |
| KLK8/KLK5 | 0.33 | 5.53 | 0.018 | 43 | 26 |
| KLK8/KLK6 | 0.10 | 7.54 | 0.006 | 22 | 26 |
| KLK8/KLK7 | 0.020 | 15.39 | 0.00008 | 22 | 26 |
| KLK8/NT4 | 0.020 | 12.46 | 0.0004 | 19 | 26 |
| KLK8/KLK10 | 0.2 | 8.16 | 0.004 | 44 | 24 |
| KLK8/KLK11 | 0.02 | 8.16 | 0.004 | 42 | 24 |
| KLK8/KLK13 | 0.1 | 13.49 | 0.0002 | 40 | 24 |
| KLK8/KLK14 | 0.050 | 8.16 | 0.004 | 39 | 24 |

TABLE 15

| Variable | Cox model HR | Cox model 95% CI | Cox model P |
|---|---|---|---|
| stages 3 + 4 vs stages 1 + 2 | 3.753 | 1.654-8.515 | 0.0016 |
| adjusted "strong KLK8" vs weak KLK8 | 2.0152 | 0.856-5.412 | 0.1033 |
| stages 3 + 4 vs stages 1 + 2 | 3.878 | 1.712-8.784 | 0.0012 |
| adjusted "strong KLK8/KLK5" vs weak KLK8/KLK5 | 2.221 | 0.922-5.351 | 0.0752 |
| stages 3 + 4 vs stages 1 + 2 | 4.129 | 1.830-9.132 | 0.0009 |
| adjusted "strong KLK8/KLK6" vs weak KLK8/KLK6 | 0.752 | 0.299-1.889 | 0.5440 |
| stage 3 + 4 vs stage 1 + 2 | 3.824 | 1.684-8.684 | 0.0013 |
| adjusted "strong KLK8/KLK7" vs weak KLK8/KLK7 | 3.152 | 0.938-10.585 | 0.0633 |
| stages 3 + 4 vs stages 1 + 2 | 4.152 | 1.833-9.401 | 0.0006 |
| adjusted "strong KLK8/NT4" vs KLK8/NT4 | 0.851 | 0.290-2.501 | 0.7695 |
| stages 3 + 4 vs stages 1 + 2 | 3.952 | 1.742-8.964 | 0.0010 |
| adjusted "strong KLK8/KLK10" vs adjusted weak KLK8/KLK10 | 3.054 | 1.320-7.062 | 0.0091 |
| stages 3 + 4 vs stages 1 + 2 | 3.725 | 1.639-8.470 | 0.0017 |
| adjusted "strong KLK8/KLK11" vs weak KLK8/KLK11 | 3.247 | 1.352-7.797 | 0.0084 |
| stages 3 + 4 vs stages 1 + 2 | 3.268 | 1.423-7.504 | 0.0052 |
| adjusted "strong KLK8/KLK13" vs adjusted weak KLK8/KLK13 | 3.415 | 1.265-9.218 | 0.0153 |
| stages 3 + 4 vs stages 1 + 2 | 3.249 | 1.487-7.911 | 0.0039 |
| adjusted "strong KLK8/KLK14" vs weak KLK8/KLK14 | 2.178 | 0.852-5.573 | 0.1042 |

CI, confidence interval

Patients having a high value of the variable "KLK8" have lower survival than the others (log rank test, P=0.0353); however, this variable is linked to the variable "tumor stage", as is shown by the non-significant P of the adjusted variable (Table 17).

The variable "KLK8" becomes independent when it is combined in the form of a ratio with the expression levels of other kallikrein genes (P<0.05; Table 17). This is the case with the ratios KLK8/KLK10, KLK8/KLK11 and KLK8/

KLK13. These variables thus constitute adverse and independent prognostic indicators for carcinoma of the lung.

EXAMPLE 6

Demonstration of the Presence of the Transcript NT4 in the Blood of Patients Suffering from Carcinoma of the Lung Sensitive detection of latent carcinoma on the basis of the peripheral blood of patients having a carcinoma could have important prognostic or therapeutic implications. We therefore performed this experiment in order to verify that it was possible to detect the presence of NT4 transcripts in the blood and that that detection could be linked to a carcinoma of the lung.

Blood from healthy subjects and from subjects suffering from a carcinoma of the lung were taken in "PAXgene™ Blood RNA" tubes (Europe BD) then the total RNAs were prepared by means of the PAXgene Blood RNA System (Qiagen, France) according to the suppliers' recommendations. These total RNAs were retro-transcribed to cDNA according to the procedure described in Example 1. The testing for the NT4 transcript was performed by means of a "nested PCR" (2 consecutive PCRs). In the first PCR, we utilized the primers K8Not_for and K8Eco_rev described in Example 1. The reaction medium was identical to that in that example, as were the PCR conditions. However, only 30 amplification cycles were performed. For the second PCR, we utilized the primers NT4-2/6 and NT4_rev described respectively in Examples 2 and 3. The reaction medium (containing 1 µl of the first PCR) and the amplification program were identical to Example 1, apart from the fact that the primer hybridization phase was performed at 62° C. Fifty cycles were performed and 10 µl of the PCR medium were deposited onto an agarose gel dyed with ethidium bromide The results are shown in FIG. 2 which is a photograph of an electrophoresis gel thus obtained from two patients suffering from cancer and from two healthy patients.

As is shown by FIG. 2, it is not possible to detect the transcript NT4 in the blood from healthy patients. This observation indicates the absence of this transcript in normal blood cells. The transcript NT4 was detected in one of the patients suffering from a carcinoma of the lung. This approach thus makes it possible to detect the presence of circulating tumor cells in certain subjects having a carcinoma of the lung.

Bibliography

1: Etzioni R. et al., 2003, Nature Reviews Cancer, 3: 1-10
2: Pisters K M et al, 2005, J Clin Oncol, 23:3270-3278,
3: Bhattacharjee A. et al., 2001, Proc Natl Acad Sci USA, 98: 13790-13795,
4: Garber M. E. et al., 2001, Proc Natl Acad Sci USA, 98: 13784-13789,
5: Planque C. et al., 2005, Biochemical and Biophysical Research Communications, 329: 1260-1266,
6: Dong Y. et al, 2001, Clin Cancer Res, 7: 2363-2371,
7: Dong Y. et al, 2003, Clin Cancer Res, 9: 1710-1720,
8: Yoshida S. et al, 1998, Gene, 213: 9-16,
9: Mitsui S. et al, 1999, Bur J Biochem, 260: 627-634,
10: Magklara A. et al, 2001, Clin Cancer Res, 7: 806-811,
11: P. E. Nielsen et al, 1991, Science, 254: 1497-1500,
12: Kricka et al., 1999, Clinical Chemistry, no 45(4): 453-458,
13: Keller G. H. et al., 1993, DNA Probes, 2nd Ed., Stockton Press, sections 5 and 6, p. 173-249,
14: Tyagi & Kramer, 1996, Nature biotech, 14:303-308
15: M. Chee et al., 1996, Science, 274: 610-614,
16: A. Caviani Pease et al., 1994, Proc. Natl. Acad. Sci. USA, 91: 5022-5026,
17: G. Ramsay, 1998, Nature Biotechnology, 16: 40-44,
18: F. Ginot, 1997, Human Mutation, 10:1-10,
19: J. Cheng et al, 1996, Molecular diagnosis, 1(3): 183-200,
20: T. Livache et al, 1994, Nucleic Acids Research, 22(15): 2915-2921,
21: J. Cheng et al, 1998, Nature Biotechnology, 16: 541-546,
22: Boom R. et al., 1990, J. Clin. Microbiol., 28(3): 495-503,
23: Levison P R et al., 1998, J. Chromatography, p. 337-344,
24: Mountain, C. F., 1997, Chest, 111: 1710-1717.

The invention claimed is:

1. A method for determining a likelihood of survival of a human patient having non-small cell bronchial carcinoma, the method comprising:
   obtaining a lung tissue sample containing nucleic acids from the human patient;
   assaying the nucleic acids to determine a quantity Q1 of a major alternative transcript of a KLK8 gene encoding kallikrein 8, wherein the transcript is an NT3 transcript consisting of SEQ ID NO: 5; and
   determining that the human patient has a decreased likelihood of survival of non-small cell bronchial carcinoma based on an increase in Q1 in the sample as compared to a predetermined threshold value.

2. The method of claim 1, further comprising detecting an NT1 transcript consisting of SEQ ID NO: 3 encoding kallikrein KLK8.

3. The method of claim 1, further comprising detecting an alternative transcript selected from the group consisting of:
   NT2 consisting of SEQ ID NO: 4,
   NT4 consisting of SEQ ID NO: 6,
   NT5 consisting of SEQ ID NO: 7, and
   NT6 consisting of SEQ ID NO: 8.

4. The method of claim 2, wherein:
   assaying the nucleic acids further comprises determining a quantity of the NT1 transcript of the gene KLK8 in the same biological sample; and
   determining that the human patient has a decreased likelihood of survival of non-small cell bronchial carcinoma based on an increase in the quantity of the NT1 transcript of the KLK8 gene and an increase in Q1 in the sample as compared to a predetermined threshold value.

5. The method of claim 1, wherein the method further comprises detecting at least one transcript of a gene encoding another kallikrein selected from the group consisting of KLK5, KLK6, KLK7, KLK10, KLK11, KLK13, and KLK14.

6. The method of claim 5, wherein:
   assaying the nucleic acids further comprises:
      determining a quantity of the transcript of the gene encoding the other kallikrein in the same sample (Q2), and
      calculating a ratio Q1/Q2 or Q2/Q1; and
   determining that the human patient has a decreased likelihood of survival of non-small cell bronchial carcinoma based on an increase in said ratio as compared to a predetermined threshold value.

7. The method of claim 1, wherein the assaying step is carried out using a diagnostic kit containing a binding partner of the NT3 transcript.

* * * * *

SEQUENCE LISTING

<160> NUMBER OF SEQ ID NOS: 32

<210> SEQ ID NO 1
<211> LENGTH: 30
<212> TYPE: DNA
<213> ORGANISM: Artificial sequence
<220> FEATURE:
<223> OTHER INFORMATION: Amplification primer

<400> SEQUENCE: 1
tggagggcgg ccgcatggga cgcccccgac                30

<210> SEQ ID NO 2
<211> LENGTH: 27
<212> TYPE: DNA
<213> ORGANISM: Artificial sequence
<220> FEATURE:
<223> OTHER INFORMATION: Amplification primer

<400> SEQUENCE: 2
tcctagatat cgcccttgct gcctatg                27

```
<210> SEQ ID NO 3
<211> LENGTH: 806
<212> TYPE: DNA
<213> ORGANISM: Artificial sequence
<220> FEATURE:
<223> OTHER INFORMATION: NT1 Transcrit ok Kallicreine 8

<400> SEQUENCE: 3
tggaagggcg gccgcatggg acgccccga cctcgtgcgg ccaagacgtg gatgttcctg      60
ctcttgctgg ggggagcctg ggcaggacac tccagggcac aggaggacaa ggtgctgggg    120
ggtcatgagt gccaaccca ttcgcagcct tggcaggcgg ccttgttcca gggccagcaa    180
ctactctgtg gcggtgtcct tgtaggtggc aactgggtcc ttacagctgc ccactgtaaa   240
aaaccgaaat acacagtacg cctgggagac cacagcctac agaataaaga tggcccagag   300
caagaaatac ctgtggttca gtccatccca caccctgct acaacagcag cgatgtggag    360
gaccacaacc atgatctgat gcttcttcaa ctgcgtgacc aggcatccct ggggtccaaa   420
gtgaagccca tcagcctggc agatcattgc acccagcctg ccagaagtg caccgtctca     480
ggctggggca ctgtcaccag tccccgagag aattttcctg acactctcaa ctgtgcagaa   540
gtaaaaatct ttccccagaa gaagtgtgag gatgcttacc cggggcagat acagatggc    600
atggtctgtg caggcagcag caaaggggct gacacgtgcc agggcgattc tggaggcccc   660
ctggtgtgtg atggtgcact ccagggcatc acatcctggg gctcagaccc ctgtgggagg   720
tccgacaaac tggcgtctta taccaacatc tgccgctacc tggactggat caagaagatc   780
ataggcagca agggcgatat ctagga                                        806

<210> SEQ ID NO 4
<211> LENGTH: 940
<212> TYPE: DNA
<213> ORGANISM: Artificial sequence
<220> FEATURE:
<223> OTHER INFORMATION: NT2 Transcrit of Kallicreine 8

<400> SEQUENCE: 4
tggaaggcgg ccgcatggga cgccccgac ctcgtgcggc caagacgtgg atgttcctgc     60
tcttgctggg gggagcctgg gcagcgtgtg gaagcctgga cctcctcact aagttgtatg   120
cggagaactt gccgtgtgtc catttgaacc cacagtggcc ttcccagccc tcgcactgcc   180
ccagagggtg gcgatccaac cctctccctc ctgctgcagg acactccagg gcacaggagg   240
acaaggtgct ggggggtcat gagtgccaac cccattcgca gccttggcag gcggccttgt   300
tccagggcca gcaactactc tgtggcggtg tccttgtagg tggcaactgg gtccttacag   360
ctgcccactg taaaaaaccg aaatacacag tacgcctggg agaccacagc ctacagaata   420
aagatggccc agagcaagaa atacctgtgg ttcagtccat cccacacccc tgctacaaca   480
gcagcgatgt ggaggaccac aaccatgatc tgatgcttct tcaactgcgt gaccaggcat   540
ccctggggtc caaagtgaag cccatcagcc tggcagatca ttgcacccag cctgccaga   600
agtgcaccgt ctcaggctgg ggcactgtca ccagtccccg agaattttt cctgacactc    660
tcaactgtgc agaagtaaaa atctttcccc agaagaagtg tgaggatgct tacccggggc   720
agatcacaga tggcatggtc tgtgcaggca gcagcaaagg ggctgacacg tgccagggcg   780
attctggagg ccccctggtg tgtgatggtg cactccaggg catcacatcc tggggctcag   840
acccctgtgg gaggtccgac aaacctggcg tctataccaa catctgccgc tacctggact   900
ggatcaagaa gatcataggc agcaagggcg atatctagga                         940
```

```
<210> SEQ ID NO 5
<211> LENGTH: 383
<212> TYPE: DNA
<213> ORGANISM: Artificial sequence
<220> FEATURE:
<223> OTHER INFORMATION: NT3 Transcrit of Kallicreine 8

<400> SEQUENCE: 5
tggaaggcgg ccgcatggga cgcccccgac ctcgtgcggc caagacgtgg atgttcctgc      60
tcttgctggg gggagcctgg gcagagaatt ttcctgacac tctcaactgt gcagaagtaa     120
aaatctttcc ccagaagaag tgtgaggatg cttacccggg gcagatcaca gatggcatgg     180
tctgtgcagg cagcagcaaa ggggctgaca cgtgccaggc cgattctgga ggcccctgg      240 tgtgtgatgg tgcactccag ggcatcacat cctggggctc agaccctgt gggaggtccg      300 acaaacctgg cgtctatacc aacatctgcc gctacctgga ctggatcaag aagatcatag     360
gcagcaaggg cgatatctag gga                                             383

<210> SEQ ID NO 6
<211> LENGTH: 248
<212> TYPE: DNA
<213> ORGANISM: Artificial sequence
<220> FEATURE:
<223> OTHER INFORMATION: NT4 Transcrit of Kallicreine 8

<400> SEQUENCE: 6
tggaaggcgg ccgcatggga cgcccccgac ctcgtgcggc caagacgtgg atgttcctgc      60
tcttgctggg gggagcctgg gcagggcgat tctggaggcc ccctggtgtg tgatggtgca     120
ctccagggca tcacatcctg ggctcagac ccctgtggga ggtccgacaa acctggcgtc      180
tataccaaca tctgccgcta cctggactgg atcaagaaga tcataggcag caagggcgat     240
atctagga                                                              248

<210> SEQ ID NO 7
<211> LENGTH: 645
<212> TYPE: DNA
<213> ORGANISM: Artificial sequence
<220> FEATURE:
<223> OTHER INFORMATION: NT5 Transcrit of Kallicreine 8

<400> SEQUENCE: 7
tggaaggcgg ccgcatggga cgcccccgac ctcgtgcggc caagacgtgg atgttcctgc      60
tcttgctggg gggagcctgg gcaggaaata cacagtacgc ctgggagacc acagcctaca     120
gaataaagat ggcccagagc aagaaatacc tgtggttcag tccatcccac acccctgcta     180
caacagcagc gatgtggagg accacaacca tgatctgatg cttcttcaac tgcgtgacca     240
ggcatccctg gggtccaaag tgaagcccat cagcctggca gatcattgca cccagcctgg     300
ccagaagtgc accgtctcag gctggggcac tgtcaccagt ccccgagaga ttttcctga     360 cactctcaac tgtgcagaag taaaaatctt tccccagaag aagtgtgagg atgcttaccc     420
ggggcagatc acagatggca tggtctgtgc aggcaacagc aaaggggctg acacgtgcca     480
gggcgattct ggaggccccc tggtgtgtga tggtgcactc cagggcatca catcctgggg     540
ctcagacccc tgtgggaggt ccgacaaacc tggcgtctat accaacatct gccgctacct     600
ggactggatc aagaagatca taggcagcaa gggcgatatc tagga                     645

<210> SEQ ID NO 8
<211> LENGTH: 542
```

<212> TYPE: DNA
<213> ORGANISM: Artificial sequence
<220> FEATURE:
<223> OTHER INFORMATION: NT6 Transcrit of Kallicreine 8

<400> SEQUENCE: 8

```
tggaaggcgg ccgcatggga cgcccccgac ctcgtgcggc ctagacgtgg atgttcctgc      60
tcttgctggg gggagcctgg gcaggacact ccagggcaca ggaggacaag gtgctggggg    120
gtcatgagtg ccaaccccat tcgcagcctt ggcaggtggc cttgttccag ggccagcaac    180
tactctgtgg cggtgtcctt gtaggtggca actgggtcct tacagctgcc cactgtaaaa    240
aaccagaatt ttcctgacac tctcaactgt gcagaagtaa aaatctttcc ccagaagaag    300
tgtgaggatg cttacccggg gcagatcaca gatggcatgg tctgtgcagg cagcagcaaa    360
ggggctgaca cgtgccaggg cgattctgga ggccccctgg tgtgtgatgg tgcactccag    420
ggcatcacat cctggggctc agaccctgt gggaggtccg acaaacctgg cgtctatacc     480
aacatctgcc gctacctgga ctggatcaag aagatcatag gcagcaaggg cgatatctag    540
ga                                                                  542
```

<210> SEQ ID NO 9
<211> LENGTH: 18
<212> TYPE: DNA
<213> ORGANISM: Artificial sequence
<220> FEATURE:
<223> OTHER INFORMATION: Amplification primer

<400> SEQUENCE: 9

```
ggagcctggg cagagaat                                                   18
```

<210> SEQ ID NO 10
<211> LENGTH: 16
<212> TYPE: DNA
<213> ORGANISM: Artificial sequence
<220> FEATURE:
<223> OTHER INFORMATION: Amplification primer

<400> SEQUENCE: 10

```
tgggcagggc gattct                                                     16
```

<210> SEQ ID NO 11
<211> LENGTH: 24
<212> TYPE: DNA
<213> ORGANISM: Artificial sequence
<220> FEATURE:
<223> OTHER INFORMATION: Amplification primer

<400> SEQUENCE: 11

```
ctaccacatc caaggaaggc agca                                            24
```

<210> SEQ ID NO 12
<211> LENGTH: 24
<212> TYPE: DNA
<213> ORGANISM: Artificial sequence
<220> FEATURE:
<223> OTHER INFORMATION: Amplification primer

<400> SEQUENCE: 12

```
gctatcaatc tgtcaatcct gtcc                                            24
```

<210> SEQ ID NO 13
<211> LENGTH: 16

```
<212> TYPE: DNA
<213> ORGANISM: Artificial sequence
<220> FEATURE:
<223> OTHER INFORMATION: Amplification primer

<400> SEQUENCE: 13
cctccagaat cgccct                                                     16

<210> SEQ ID NO 14
<211> LENGTH: 18
<212> TYPE: DNA
<213> ORGANISM: Artificial sequence
<220> FEATURE:
<223> OTHER INFORMATION: Amplification primer

<400> SEQUENCE: 14
cagtccaggt agcggcag                                                   18

<210> SEQ ID NO 15
<211> LENGTH: 23
<212> TYPE: DNA
<213> ORGANISM: Artificial sequence
<220> FEATURE:
<223> OTHER INFORMATION: Amplification primer

<400> SEQUENCE: 15
cgcggttcta ttttgttggt ttt                                             23

<210> SEQ ID NO 16
<211> LENGTH: 20
<212> TYPE: DNA
<213> ORGANISM: Artificial sequence
<220> FEATURE:
<223> OTHER INFORMATION: Amplification primer

<400> SEQUENCE: 16
ttcgctctgg tccgtcttgc                                                 20

<210> SEQ ID NO 17
<211> LENGTH: 20
<212> TYPE: DNA
<213> ORGANISM: Artificial sequence
<220> FEATURE:
<223> OTHER INFORMATION: Amplification primer

<400> SEQUENCE: 17
gccactactc cctgtcacca                                                 20

<210> SEQ ID NO 18
<211> LENGTH: 20
<212> TYPE: DNA
<213> ORGANISM: Artificial sequence
<220> FEATURE:
<223> OTHER INFORMATION: Amplification primer

<400> SEQUENCE: 18
gcatcctcgc acctttctg                                                  20

<210> SEQ ID NO 19
<211> LENGTH: 17
<212> TYPE: DNA
<213> ORGANISM: Artificial sequence
<220> FEATURE:
<223> OTHER INFORMATION: Amplification primer
```

```
<400> SEQUENCE: 19
tgatggtggt gctgagt                                                    17

<210> SEQ ID NO 20
<211> LENGTH: 19
<212> TYPE: DNA
<213> ORGANISM: Artificial sequence
<220> FEATURE:
<223> OTHER INFORMATION: Amplification primer

<400> SEQUENCE: 20
acagtggatg gataaggac                                                  19

<210> SEQ ID NO 21
<211> LENGTH: 18
<212> TYPE: DNA
<213> ORGANISM: Artificial sequence
<220> FEATURE:
<223> OTHER INFORMATION: Amplification primer

<400> SEQUENCE: 21
gagcccagat gtgacctt                                                   18

<210> SEQ ID NO 22
<211> LENGTH: 19
<212> TYPE: DNA
<213> ORGANISM: Artificial sequence
<220> FEATURE:
<223> OTHER INFORMATION: Amplification primer

<400> SEQUENCE: 22
tccttgtaaa ccttcgtgc                                                  19

<210> SEQ ID NO 23
<211> LENGTH: 17
<212> TYPE: DNA
<213> ORGANISM: Artificial sequence
<220> FEATURE:
<223> OTHER INFORMATION: Amplification primer

<400> SEQUENCE: 23
ggaccccgaa gcctatg                                                    17

<210> SEQ ID NO 24
<211> LENGTH: 17
<212> TYPE: DNA
<213> ORGANISM: Artificial sequence
<220> FEATURE:
<223> OTHER INFORMATION: Amplification primer

<400> SEQUENCE: 24
cctgagccct ggtggta                                                    17

<210> SEQ ID NO 25
<211> LENGTH: 20
<212> TYPE: DNA
<213> ORGANISM: Artificial sequence
<220> FEATURE:
<223> OTHER INFORMATION: Amplification primer

<400> SEQUENCE: 25
caggatcatc aaggggttcg                                                 20

<210> SEQ ID NO 26
<211> LENGTH: 20
<212> TYPE: DNA
```

```
<213> ORGANISM: Artificial sequence
<220> FEATURE:
<223> OTHER INFORMATION: Amplification primer

<400> SEQUENCE: 26
cattgcggtg gtctttgttg                                               20

<210> SEQ ID NO 27
<211> LENGTH: 19
<212> TYPE: DNA
<213> ORGANISM: Artificial sequence
<220> FEATURE:
<223> OTHER INFORMATION: Amplification primer

<400> SEQUENCE: 27
gtgccaacat ccaacttcg                                                19

<210> SEQ ID NO 28
<211> LENGTH: 19
<212> TYPE: DNA
<213> ORGANISM: Artificial sequence
<220> FEATURE:
<223> OTHER INFORMATION: Amplification primer

<400> SEQUENCE: 28
ccctcacagg agtctttgc                                                19

<210> SEQ ID NO 29
<211> LENGTH: 19
<212> TYPE: DNA
<213> ORGANISM: Artificial sequence
<220> FEATURE:
<223> OTHER INFORMATION: Amplification primer

<400> SEQUENCE: 29
tgggtcatca ctgctgctc                                                19

<210> SEQ ID NO 30
<211> LENGTH: 19
<212> TYPE: DNA
<213> ORGANISM: Artificial sequence
<220> FEATURE:
<223> OTHER INFORMATION: Amplification primer

<400> SEQUENCE: 30
ctcctcaggt tgtgcttgc                                                19

<210> SEQ ID NO 31
<211> LENGTH: 20
<212> TYPE: DNA
<213> ORGANISM: Artificial sequence
<220> FEATURE:
<223> OTHER INFORMATION: Amplification primer

<400> SEQUENCE: 31
ccagaagaag tgtgaggatg                                               20

<210> SEQ ID NO 32
<211> LENGTH: 19
<212> TYPE: DNA
<213> ORGANISM: Artificial sequence
<220> FEATURE:
<223> OTHER INFORMATION: Amplification primer

<400> SEQUENCE: 32
ggtatagacg ccaggtttg                                                19
```